US008801662B2

(12) United States Patent
Doshi et al.

(10) Patent No.: US 8,801,662 B2
(45) Date of Patent: Aug. 12, 2014

(54) BALLOON CATHETER PROVIDING DECREASED IRRITATION AND IMPROVED DRUG RELEASE AND DRUG PENETRATION

(75) Inventors: Manish Doshi, Surat (IN); Divyesh Sherdiwala, Surat (IN); Prakash Sojitra, Surat (IN); Ashwin Vyas, Amreli (IN); Pankaj Gandhi, Surat (IN)

(73) Assignee: Concept Medical, Inc, San Jose, CA (US)

( * ) Notice: Subject to any disclaimer, the term of this patent is extended or adjusted under 35 U.S.C. 154(b) by 0 days.

(21) Appl. No.: 12/920,812

(22) PCT Filed: May 21, 2010

(86) PCT No.: PCT/IN2010/000349
§ 371 (c)(1),
(2), (4) Date: Sep. 2, 2010

(87) PCT Pub. No.: WO2010/140163
PCT Pub. Date: Dec. 9, 2010

(65) Prior Publication Data
US 2012/0065584 A1    Mar. 15, 2012

(30) Foreign Application Priority Data

Jun. 2, 2009    (IN) .......................... 1337/MUM/2009

(51) Int. Cl.
*A61M 25/10*    (2013.01)
*B05D 7/00*    (2006.01)
*B05D 5/00*    (2006.01)
*B82Y 5/00*    (2011.01)

(52) U.S. Cl.
USPC ........ 604/103.02; 427/2.1; 427/2.3; 977/700; 977/906

(58) Field of Classification Search
USPC ......... 604/103.02; 427/2.1, 2.3; 977/700, 906
See application file for complete search history.

(56) References Cited

U.S. PATENT DOCUMENTS

| 5,102,402 | A | * | 4/1992 | Dror et al. ................ 604/103.02 |
| 5,603,991 | A | | 2/1997 | Kupiecki |
| 5,893,840 | A | * | 4/1999 | Hull et al. ................ 604/103.02 |
| 6,656,156 | B2 | | 12/2003 | Yang et al. |
| 7,048,714 | B2 | * | 5/2006 | Richter .................... 604/103.02 |
| 2003/0064965 | A1 | * | 4/2003 | Richter ........................ 514/102 |

(Continued)

OTHER PUBLICATIONS

"PCT International Search Report", Application No. PCT/IN2010/000349, (Dec. 2, 2010), 6 pages.

(Continued)

*Primary Examiner* — Quynh-Nhu H Vu
(74) *Attorney, Agent, or Firm* — Timberline Patent Law Group PLLC (57) ABSTRACT

A drug-delivering medical device for delivering a drug to a target site in a body lumen is disclosed. The drug-delivering medical device includes a balloon catheter and an inflatable balloon positioned on the balloon catheter. The inflatable balloon has a hydrophilic surface. One or more portions of the hydrophilic surface are coated with two or more nano-carriers. A nano-carrier of the two or more nano-carriers includes a drug surrounded by an encapsulating medium. As the drug is surrounded by the encapsulating medium, the surface of the nano-carrier is devoid of the drug. When the inflatable balloon is inflated upon coming in proximity to a target site in the body lumen, about 30% to 80% of the two or more nano-carriers are released from the hydrophilic surface within 15-90 seconds.

12 Claims, 8 Drawing Sheets

(56) References Cited

U.S. PATENT DOCUMENTS

| | | |
|---|---|---|
| 2007/0212386 A1* | 9/2007 | Patravale et al. .............. 424/422 |
| 2008/0118544 A1* | 5/2008 | Wang ............................ 424/423 |
| 2009/0099651 A1* | 4/2009 | Hakimi-Mehr et al. ..... 623/1.42 |
| 2009/0246252 A1* | 10/2009 | Arps et al. .................... 424/425 |
| 2011/0099789 A1* | 5/2011 | Ewing et al. ................... 29/428 |

OTHER PUBLICATIONS

Pendyala, Lakshmana et al., "Passive and Active Polymer Coatings for Intracoronary Stents: Novel Devices to Promote Arterial Healing", *Journal of Interventional Cardiology*, vol. 22, No. 1,(2009),pp. 37-48.

\* cited by examiner

| Process | CV Number | Timepoint | Animal Number | Vessel/Stent Type | |
|---|---|---|---|---|---|
| | | | | Left Iliac | Right Iliac |
| PK | N/A | 8 days | 66 | DEB | DEB |
| | N/A | | 67 | DEB | DEB |
| | N/A | | 68 | DEB | DEB |
| | N/A | 1 day | 69 | DEB | DEB |
| | N/A | | 70 | DEB | DEB |
| | N/A | | 71 | DEB | DEB |
| | N/A | 14 days | 72 | DEB | DEB |
| | N/A | | 73 | DEB | DEB |
| | N/A | | 74 | DEB | DEB |
| LM | 23640 | 28 days | 75 | Non-DEB | DEB |
| | 23641 | | 76 | DEB | Non-DEB |
| | 23642 | | 77 | Non-DEB | DEB |
| | 23643 | | 78 | DEB | Non-DEB |
| | 23644 | | 79 | Non-DEB | DEB |
| | 23645 | | 80 | DEB | Non-DEB |
| | 23646 | | 81 | Non-DEB | DEB |
| | 23647 | | 82 | DEB | Non-DEB |

FIG. 3

| Parameter | Animal | Mean | Std. Deviation | P-Value Kruskal Wallis Test |
|---|---|---|---|---|
| Luminal Area Average | Control | 4,68 | 1,92 | 0.5 |
| | Sirolimus | 4,41 | 1,53 | |
| | Paclitaxel | 3,71 | 1,50 | |
| Stent Area Average | Control | 6,95 | 1,10 | 0.3 |
| | Sirolimus | 6,24 | 1,11 | |
| | Paclitaxel | 7,07 | 0,68 | |
| NIH average | Control | 2,27 | 1,30 | 0.048 |
| | Sirolimus | 1,83 | 0,75 | |
| | Paclitaxel | 3,36 | 1,07 | |
| NIH Percent Obstr Average | Control | 0,34 | 0,21 | 0.2 |
| | Sirolimus | 0,31 | 0,15 | |
| | Paclitaxel | 0,48 | 0,17 | |

FIG. 4

| Parameter | Animal | Mean | Std. Deviation | P-Value Kruskal Wallis Test |
|---|---|---|---|---|
| Luminal Area Median | Control | 4,74 | 1,89 | 0.5 |
| | Sirolimus | 4,39 | 1,51 | |
| | Paclitaxel | 3,66 | 1,53 | |
| Stent Area Median | Control | 6,94 | 1,12 | 0.4 |
| | Sirolimus | 6,20 | 1,11 | |
| | Paclitaxel | 6,98 | 0,55 | |
| NIH Median | Control | 2,27 | 1,30 | 0.09 |
| | Sirolimus | 1,80 | 0,74 | |
| | Paclitaxel | 3,37 | 1,26 | |
| NIH Percent Obstr Median | Control | 0,33 | 0,21 | 0.2 |
| | Sirolimus | 0,30 | 0,14 | |
| | Paclitaxel | 0,49 | 0,19 | |

FIG. 5

| Parameter | Animal | Mean | Std. Deviation | P-Value Kruskal Wallis Test |
|---|---|---|---|---|
| Luminal Area Minimal | Control | 4,20 | 1,97 | 0.6 |
| | Sirolimus | 3,89 | 1,60 | |
| | Paclitaxel | 3,12 | 1,60 | |
| Stent Area Minimal | Control | 6,61 | 0,89 | 0.5 |
| | Sirolimus | 5,93 | 1,14 | |
| | Paclitaxel | 6,43 | 0,80 | |
| NIH Minimal | Control | 1,93 | 1,37 | 0.3 |
| | Sirolimus | 1,33 | 0,75 | |
| | Paclitaxel | 2,41 | 1,27 | |
| NIH Percent Obstr Minimal | Control | 0,30 | 0,22 | 0.5 |
| | Sirolimus | 0,23 | 0,13 | |
| | Paclitaxel | 0,36 | 0,17 | |

FIG. 6

| Parameter | Animal | Mean | Std. Deviation | P-Value Kruskal Wallis Test |
|---|---|---|---|---|
| Luminal Area Maximal | Control | 4,99 | 1,98 | 0.7 |
| | Sirolimus | 4,98 | 1,54 | |
| | Paclitaxel | 4,40 | 1,41 | |
| stent Area Maximal | Control | 7,28 | 1,26 | 0.4 |
| | Sirolimus | 6,64 | 1,16 | |
| | Paclitaxel | 7,92 | 1,38 | |
| NIH Maximal | Control | 2,66 | 1,25 | 0.02 |
| | Sirolimus | 2,32 | 0,93 | |
| | Paclitaxel | 4,39 | 1,21 | |
| NIH Percent Obstr Maximal | Control | 0,40 | 0,22 | 0.2 |
| | Sirolimus | 0,39 | 0,18 | |
| | Paclitaxel | 0,59 | 0,19 | |

BALLOON CATHETER PROVIDING DECREASED IRRITATION AND IMPROVED DRUG RELEASE AND DRUG PENETRATION

FIELD OF THE INVENTION

The invention generally relates to a medical device for administrating a drug to a target site in a body lumen. More specifically, the invention relates to a drug-delivering inflatable balloon coated with nano-carriers of one or more drugs for efficient delivery of the one or more drugs to the target site in a blood vessel.

BACKGROUND OF THE INVENTION

Drug-delivering insertable medical devices are used for localized delivery of a drug to a target site in a blood vessel. Drug Eluting Balloon (DEB) is one such drug-delivering insertable medical device. Although, widely used, the DEBs are associated with use of polymers for loading the drug on the surface of the DEBs. The polymers used may cause inflammation at the target site. To avoid the inflammation caused by the polymers, the drug may be loaded on the surface of the DEB without using the polymers. However, such polymer-free approaches known in the art are based on surface modification of the DEB.

Additionally, the DEB comes in contact with the target site in the blood vessel for a very short period, generally, ranging from 30 seconds to 90 seconds. The required amount of the drug loaded on the DEB may not be released from the surface of the DEB within such a short period. Therefore, a higher amount of the drug has to be loaded on the DEB as compared to the amount of the drug actually required to be delivered. As the higher amount of the drug is loaded on the DEB, a substantial amount of the drug may remain on the surface of the DEB after the DEB is withdrawn from the target site. The remaining amount of the drug present on the DEB may get washed away in the blood stream while the DEB is being withdrawn through the blood vessel thereby producing unwanted side effects.

Further, micro-sized drug particles are coated on the current DEBs. The micro-sized particles of the drug may not penetrate tissues at the target site efficiently. Thus, the current DEBs may not exhibit an efficient in-tissue diffusion of the drug.

Therefore, there is a need in the art for a DEB that can efficiently deliver the drug to the target site in the blood vessel within a short period for which the DEB comes in contact with the target site. In addition, there is a need in the art for a DEB that can efficiently deliver drug to the maximum area of a lesion and provide for enhance bioavailability with an optimum amount of the drug loaded on the drug-delivering balloon.

BRIEF DESCRIPTION OF FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the invention.

DETAILED DESCRIPTION OF THE INVENTION

Before describing in detail embodiments that are in accordance with the invention, it should be observed that the embodiments reside primarily in combinations of components of a drug-delivering insertable medical device for localized delivery of a drug to a target site in a blood vessel. Accordingly, the components have been described to include only those specific details that are pertinent to understanding the embodiments of the invention so as not to obscure the disclosure with details that will be readily apparent to those of ordinary skill in the art having the benefit of the description herein.

In this document, the terms "comprises", "comprising" or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used herein for describing the invention have same meanings as would be understood by a person skilled in the art.

Generally speaking, pursuant to various embodiments, the invention discloses a drug-delivering medical device for delivering a drug to a target site in a body lumen. The body lumen may be one of a blood vessel, a urethra, an esophagus, a ureter and a bile duct. The drug-delivering medical device is used to treat a medical condition associated with the body lumen. The medical condition may be, for example, atherosclerosis, a blocked artery, restenosis, plaque accumulation in a blood vessel and thrombus formation in the blood vessel.

The drug-delivering medical device includes a balloon catheter and an inflatable balloon positioned on the balloon catheter. The inflatable balloon has a hydrophilic surface. One or more portions of the hydrophilic surface are coated with two or more nano-carriers. A nano-carrier of the two or more nano-carriers includes a drug surrounded by an encapsulating medium. The encapsulating medium may be one or more of a biological agent, a blood excipient and a phospholipid. As the drug is surrounded by the encapsulating medium, the surface of the nano-carrier is devoid of the drug. When the inflatable balloon is inflated upon coming in proximity to the target site in the body lumen, about 30% to 80% of the two or more nano-carriers are released from the hydrophilic surface within 15 to 90 seconds.

The drug-delivering medical device may be a balloon catheter assembly generally used for Percutaneous Transluminal Angioplasty (PTA). In an embodiment, the drug-delivering medical device is a balloon catheter assembly generally used for Percutaneous Transluminal Coronary Angioplasty (PTCA). The balloon catheter assembly essentially includes a balloon catheter and an inflatable balloon mounted on the balloon catheter. Additionally, the balloon catheter assembly may include one or more catheter tubes, one or more guide wires, a fluid supply for inflating the inflatable balloon, and any other component that may be necessary for functioning of the balloon catheter assembly for delivering the two or more nano-carriers to the target site. As the invention primarily resides in the inflatable balloon coated with the two or more nano-carriers, the functioning and components of the balloon catheter assembly other than the inflatable balloon are not disclosed in detail.

The inflatable balloon may be any balloon that is generally used in one of the PTA and the PTCA and that may also be used to deliver the two or more nano-carriers to the target site in the body lumen. For example, the inflatable balloon may be an angioplasty balloon.

The inflatable balloon has a hydrophilic surface. The hydrophilic surface may be a layer of one or more hydrophilic substances coated on the surface of the inflatable balloon, generally, to reduce the friction of the inflatable balloon with the walls of the body lumen when the inflatable balloon is moved in the body lumen. In accordance with various embodiments, the one or more hydrophilic substances may be selected from the hydrophilic substances known in the art without departing from the scope of the invention. For example, the one or more hydrophilic substances may be selected from, one or more of, but are not limited to, polyalkylene glycols, alkoxy polyalkylene glycols, copolymers of methylvinyl ether and maleic acid poly(vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate and at least one antiblock agent.

One or more portions of the hydrophilic surface are coated with the two or more nano-carriers. The two or more nano-carriers coated on the one or more portions of the hydrophilic surface are released rapidly as compared to the release of nano-carriers from the surface of a balloon without hydrophilic coating. Thus, a burst release of the two or more nano-carriers from the hydrophilic surface may be achieved within a short period for which the inflatable balloon comes in contact with the target site in the body lumen. In an exemplary embodiment, about 70% to 80% of the two or more nano-carriers are released from the hydrophilic surface within about 60 seconds when the inflatable balloon is inflated upon coming in proximity to the target site.

According to various embodiments, the hydrophilic surface may further have one or more exposed hydrophilic surfaces. The one or more exposed hydrophilic surfaces may be created at one or more desired portions of the inflatable balloon by not coating the two or more nano-carriers on the one or more desired portions. In other words, the two or more nano-carriers are coated on the entire hydrophilic surface except the one or more exposed hydrophilic surfaces. In an embodiment, the one or more exposed hydrophilic surfaces are created at one or more of one or more portions of a distal end of the hydrophilic surface and one or more portions of a proximal end of the hydrophilic surface. The one or more exposed hydrophilic surfaces facilitate dissolution of the one or more hydrophilic substances present in the one or more exposed hydrophilic surfaces upon coming in contact with the blood at the target site. In response to the dissolution of the one or more hydrophilic substances present in the one or more exposed hydrophilic surfaces, the one or more hydrophilic substances present in the hydrophilic surface may also get dissolved in the blood resulting into release of the two or more nano-carriers from the hydrophilic surface. Thus, the one or more exposed hydrophilic surfaces facilitate the release of the two or more nano-carriers from the inflatable balloon.

The inflatable balloon further has two or more nano-carriers coated on the one or more portions of the hydrophilic surface. A nano-carrier of the two or more nano-carriers includes a drug surrounded by an encapsulating medium. The drug may include nano-crystals of the drug. The nano-crystals of the drug may have an average diameter ranging from 1 nm to 1500 nm. Further, the nano-crystals of the drug may have two or more different average diameters. Alternatively, the drug may include one or more of, nano-sized particles, nano-spheres, liposomes, nano-capsules, dendrimers, and any other similar form of the drug that has nano-dimensions.

The drug may be, one or more of, but are not limited to, an anti-proliferative agent, an anti-inflammatory agent, an anti-neoplastic agent, an anti-coagulant agent, an anti-fibrin agent, an antithrombotic agent, an anti-mitotic agent, an antibiotic agent, an anti-allergic agent and an antioxidant, an anti-proliferative agent, estrogens, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, vitamins, anti-platelet aggregating agent and genetically engineered epithelial cells.

The drug may be, for example, but are not limited to, one or more of sirolimus, tacrolimus, paclitaxel, clobetasol, dexamethasone, genistein, heparin, 17 beta-estadiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin, sodium heparin, a low molecular weight heparin, a heparinoid, hirudin, argatroban, forskolin, vapiprost, prostacyclin, a prostacyclin analogue, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, a serotonin blocker, a steroid, a thioprotease inhibitor, triazolopyrimidine, a nitric oxide or nitric oxide donor, a super oxide dismutase, a super oxide dismutase mimetic, estradiol, aspirin, angiopeptin, captopril, cilazapril, lisinopril, permirolast potassium, alpha-interferon, bioactive RGD and any salts or analogues thereof.

In accordance with various embodiments, the drug is completely surrounded by the encapsulating medium and thus the surface of the nano-carrier is devoid of any free drug. Therefore, a direct contact of the drug with the surface of the inflatable balloon is avoided. Further, the drug comes in contact with the tissues of the target site only when the nano-carrier penetrates into tissues of the target site and the encapsulating medium is dissolved. Thus, direct exposure of the drug to the tissues of the target site and the surface of the inflatable is prevented due to the presence of the encapsulating medium.

The encapsulating medium may be one or more of, a biological agent, a blood excipient and a phospholipid. Alternatively, the encapsulating medium may be one or more of, but not are limited to, one or more biological agents, one or more blood excipients, one or more phospholipids and one or more excipients.

In an exemplary embodiment, the encapsulating medium may be a biological agent. The biological agent may include nano-particles of the biological agent. The nano-particles of the biological agent may have an average diameter ranging from 1 nm to 1500 nm. Further, the nano-particles of the biological agent may have two or more different average diameters. Alternatively, the biological agent may include one or more of, nano-sized particles, nano-spheres, liposomes, nano-capsules, dendrimers, and any other similar form of the biological agent that has nano-dimensions.

The biological agent may be one or more of, but are not limited to, drug carriers, excipients, blood components, excipients derived from blood, naturally occurring phospholipids, solid lipid nano-particles, phospholipids obtained from a living animal, synthetically derived phospholipids, lipoids, vitamins and sugar molecules. The biological agent may include, for example, steroids, vitamins, estradiol, esterified fatty acids, non esterified fatty acids, glucose, inositol, L-lactate, lipoproteins, carbohydrates, tricalcium phosphate, precipitated calcium phosphate, calcium phoshate tribasic, substances derived from at least one of human, egg and soybean, phospholipon 80H, phospholipon 90H, Lipoids S75, Lipoids E80, Intralipid 20, Lipoid EPC, Lipoids E75, lipids obtained from egg, lipids obtained from soya, phosphatidylcholine, phosphatidylglycerol, phosphatidylinositol, phosphatidylserine, phosphatidic acid, cardiolipin, and phosphatidylethanolamine.

In another exemplary embodiment, the encapsulating medium may be a phospholipid. The phospholipid may include nano-particles of the phospholipid. The nano-particles of the phospholipid may have an average diameter ranging from 1 nm to 1500 nm. Further, the nano-particles of the phospholipid may have two or more different average diameters. Alternatively, the phospholipid may include one or more of, nano-sized particles, nano-spheres, liposomes, nano-capsules, dendrimers, and any other similar form of the phospholipid that has nano-dimensions. The phospholipid may be one or more of, but are not limited to, lipids obtained from egg, lipids obtained from soya, phosphatidylcholine, phosphatidylglycerol, phosphatidylinositol, phosphatidylserine, phosphatidic acid, cardiolipin, and phosphatidylethanolamine.

In yet another exemplary embodiment, the encapsulating medium may be a blood excipient. The blood excipient may include nano-particles of the blood excipient. The nano-particles of the blood excipient may have an average diameter ranging from 1 nm to 1500 nm. Further, the nano-particles of the blood excipient may have two or more different average diameters. Alternatively, the blood excipient may be, one or more of, nano-sized particles, nano-spheres, liposomes, nano-capsules, dendrimers, and any other similar form of the blood excipient that has nano-dimensions. The blood excipient may be one or more excipients found in the blood that may be manufactured synthetically. The blood excipient may be one or more of, but are not limited to, steroids, vitamins, estradiol, esterified fatty acids, non-esterified fatty acids, glucose, inositol, L-lactate, lipids, lipoproteins, phospholipid, carbohydrates, tricalcium phosphate, precipitated calcium phosphate, and calcium phoshate tribasic.

The blood excipient and the biological agent are soluble at a pH below 7.4. Therefore, when the two or more nano-carriers come in contact with the tissues of the target site, the biological agent and the blood excipient get dissolved in the blood. The dissolution of the biological agent and the blood excipient results in the release of the drug from the two or more nano-carriers at the target site. Thus, a pH dependent release of the drug from the two or more nano-carriers is achieved.

Further, as the encapsulating medium is one or more of the biological agent, the blood excipient and the phospholipid, the two or more nano-carriers exhibit an affinity for the tissues of the target site. Such an affinity facilitates efficient transferring of the two or more nano-carriers from the hydrophilic surface of the inflatable balloon to the target. Further, the one or more of the biological agent and the phospholipid exhibit a property of stabilizing the drug present in the nano-carrier of the two or more nano-carriers.

The two or more nano-carriers may have an average diameter ranging from 10 nm to 1500 nm. Alternatively, two or more nano-carriers may have two or more average diameters. The two or more average diameter may range from 1 nm to 1500 nm.

In accordance with various embodiments, the two or more nano-carriers may be prepared by using the methods known in the art. For example, one or more of the nano-crystals of the drug, the nano-particles of the biological agent, the nano-particles of the phospholipid and the nano-particles of the blood excipient may be obtained by using one or more of, but are not limited to, high-pressure homogenization, spray drying, high-speed homogenization, ball milling, pulverization, sol-gel methods, hydrothermal methods, spray pyrolysis method and the like.

The nano-crystals of the drug are further encapsulated by the nano-particles of one or more of the biological agent, the phospholipid and the blood excipient to obtain the two or more nano-carriers by using methods known in the art. An average diameter of the two or more nano-carriers thus obtained may range from 1 nm to 1500 nm. Subsequently, upon obtaining the two or more nano-carriers, the two or more nano-carriers may be coated on the hydrophilic surface of the drug-delivering insertable medical device using the methods and techniques known in the art.

In an exemplary embodiment, in order to obtain the nano-crystals of the drug, a predetermined amount of the drug may be added into a solvent followed by a surfactant. For example, in order to obtain the nano-crystals of sirolimus, a predetermined amount of sirolimus may be added into water followed by Tween 80. A solution of the drug thus obtained may then be subjected to a high speed homogenization at a predetermined rpm for a predetermined time. The predetermined rpm and the predetermined time may be selected based on a desired average diameter of the nano-crystals of the drug. In response to subjecting the solution of the drug to the high-speed homogenization, at the predetermined rpm and for the predetermined time, a solution of the nano-crystals of the drug is obtained.

Similarly, a predetermined amount of the biological agent, for example, soya phospholipid, may be added into a solvent followed by a surfactant. A solution of the biological agent thus obtained may then be subjected to a high speed homogenization at a predetermined rpm for a predetermined time. The predetermined rpm and the predetermined time may be selected based on a desired average diameter of the nano-particles of the biological agent. In response to subjecting the solution of the biological agent to the high-speed homogenization, at the predetermined rpm and for the predetermined time, a solution of the nano-particles of the biological agent is obtained.

Subsequently, the solution of the nano-crystals of the drug is added to the solution of the nano-particles of the biological agent to form a mixture. The mixture is then subjected to high-speed homogenization at a predetermined rpm for a predetermined time. In response to subjecting the mixture to the high-speed homogenization, at the predetermined rpm and for the predetermined time, the nano-crystals of the drug are encapsulated with the nano-particles of the biological agent to form the two or more nano-carriers. Thus, a solution of the two or more nano-carriers may be obtained.

Thereafter, the solution of the two or more nano-carriers may be extracted with one or more organic solvent (e.g. methanol, dichloromethane, and the like.) to remove any free form of one or more of the biological agent and the drug. A solution resulting from the extraction with one or more organic solvents may then be used to coat the two or more nano-carriers on the hydrophilic surface of the inflatable balloon. The two or more nano-carriers may be coated on the hydrophilic surface of the inflatable balloon by using methods and equipments known in the art. For example, the two or more nano-carriers may be coated on the hydrophilic surface of the inflatable balloon by using one or more of, but are not limited to, a spray coating technique and atomization technique. Further, the two or more nano-carriers may be coated on the hydrophilic surface of the inflatable balloon when the balloon is in a folded configuration and an unfolded configuration.

In an embodiment, the hydrophilic surface of the inflatable balloon is coated with the two or more nano-carriers with an average diameter of 800 nm. The hydrophilic surface further has the one or more exposed hydrophilic surface at a proximal end and a distal end of the hydrophilic surface. In other words, portions at the proximal end and the distal end are not coated with the two or more nano-carriers. A nano-carrier of the two or more nano-carriers includes nano-crystals of sirolimus surrounded by one or more of tricalcium phosphate and soya phospholipid. When the inflatable balloon is inflated upon coming in proximity to the target site in the blood vessel, about 70% to 80% of the two or more nano-carriers are released from the hydrophilic surface of the inflatable balloon. The two or more nano-carriers are then absorbed by tissues at the target site.

In an exemplary embodiment, the inflatable balloon is used for treating the medical condition associated with a blood vessel. The blood vessel may be one of, for example, a coronary artery, a peripheral artery, a carotid artery, a renal artery, an illiac artery, arteries below a knee, and a vein. The blood vessel includes two or more layers of the tissues. The two or more layers of the tissues may be an intima layer, a media layer and an adventitia layer. The intima layer is an innermost layer of tissues of the blood vessel that is in direct contact with the blood flow through the blood vessel. The media layer is a layer of tissues of the blood vessel that is beneath the intima layer. Whereas, the adventitia layer is a layer of tissues of the blood vessel that is beneath the media layer.

Upon being released from the hydrophilic surface of the inflatable balloon, the nano-carrier of the two or more nano-carriers may penetrate the intima layer directly through inter-tissue pores present in the intima layer. Whereas, the nano-carrier of the two or more nano-carriers may penetrate the media layer by passing through the inter-tissue pores present in the intima layer and a vasa vasorum associated with the media layer. Similarly, the nano-carrier of the two or more nano-carriers may penetrate the adventitia layer by passing through the inter-tissue pores present in the intima layer, the vasa vasorum associated with the media layer and a vasa vasorum associated with the adventitia layer. The inter-tissue pores present in the intima layer, the vasa vasorum associated with the media layer and the vasa vasorum associated with the adventitia layer have different internal diameters. Therefore, penetration of the nano-carrier of the two or more nano-carriers into one or more of the intima layer, the media layer and the adventitia layer depends upon an average diameter associated with the two or more nano-carriers.

In another embodiment, the two or more nano-carriers include, a first set of nano-carriers, a second set of nano-carriers, and a third set of nano-carriers. The first set of nano-carriers has a first average diameter suitable for penetrating the intima layer through the inter-tissue pores present in the intima layer. The second set of nano-carriers have a second average diameter suitable for penetrating the media layer through the vasa vasorum associated with the media layer and the inter-tissue pores present in the intima layer. The third set of nano-carriers have a third diameter suitable for penetrating the adventitia layer through the inter-tissue pores present in the intima layer, the vasa vasorum associated with the media layer and the vasa vasorum associated with the adventitia layer.

The first average diameter may range from 800 nm to 1500 nm, the second average diameter may range from 300 nm to 800 nm and the third average diameter may range from 10 nm to 300 nm. In an embodiment, the first average diameter is 1000 nm, the second average diameter is 700 nm and the third average diameter is 200 nm. The first average diameter, the second average diameter and the third average diameter may be varied to meet a particular therapeutic need without departing from the scope of the invention.

The first set of nano-carriers with the first average diameter may include about 10% to 60% of the two or more nano-carriers. Whereas, the second set of nano-carriers with the second average diameter may include about 20% to 70% of the two or more nano-carriers and the third set of nano-carriers with the third average diameter may include about 30% to 80% of the two or more nano-carriers. Alternatively, the first set of nano-carriers, the second set of nano-carriers and the third set of nano-carriers may include about 15% to 90%, 10% to 85%, and 5% to 85% of the two or more nano-carriers, respectively.

When the two or more nano-carriers are released from the hydrophilic surface of the inflatable balloon, the first set of nano-carriers penetrate the media layer through the inter-tissue pores present in intima layer. The second set of nano-carriers penetrate the media layer through the vasa vasorum associated with the media layer and the inter-tissue pores present in the intima layer. Whereas, the third set of nano-carriers penetrate the adventitia layer through the vasa vasorum associated with the adventitia layer, the vasa vasorum associated with the media layer and the inter-tissue pores present in the intima layer. Thus, a size dependent penetration of the two or more nano-carriers is achieved.

In yet another embodiment, the drug present in the third set of nano-carriers may be different from a drug present in the second set of nano-carriers and the drug present in the second set of nano-carriers may be different from a drug present in the first set of nano-carriers. In other words, the drugs present in each of the first set of nano-carriers, the second set of nano-carriers and the third set of nano-carriers may be different. For example, the drug present in the third set of nano-carriers may be one or more of an anti-inflammatory agent and an anti-thrombogenic agent. The second set of nano-carriers may include an anti-proliferative agent. Whereas, the first set of the nano-carriers may include, for example, a pro-healing agent. Further, the drug present in the one or more of the first set of the nano-carriers, the second set of the nano-carriers and the third set of nano-carriers may be selected from one or more of, but not are limited to, an anti-neoplastic agent, an anti-coagulant agent, an anti-fibrin agent, an antithrombotic agent, an anti-mitotic agent, an antibiotic agent, an anti-allergic agent and an antioxidant, estrogens, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, vitamins, anti-platelet aggregating agent and genetically engineered epithelial cells without departing from the scope of the invention.

The third set of nano-carriers have a smallest average diameter among the first set of nano-carriers, the second set of nano-carriers and the third set of the nano-carriers. Therefore, the time required for the third set of nano-carriers to release from the hydrophilic surface upon coming in proximity of the target site is less than the time required for the second set of nano-carriers and the first set of nano-carriers to release from the outer surface. Thus, the third set of nano-carriers exhibit a rapid rate of release from the hydrophilic surface. Whereas, the second set of nano-carriers and the third set of nano-carriers exhibit slower rates of release from the hydrophilic surface as compared with the rate of release of the third set of nano-carriers.

Additionally, because of the presence of one or more of the biological agent, the phospholipid, and the blood excipient in the two or more nano-carriers, the two or more nano-carriers exhibit an affinity for the tissues of the target site. Further, owing to the capability of the two or more nano-carriers to penetrate the one or more layers of the blood vessel, nano-carriers with a smallest average diameter penetrate up to the adventitia layer. The nano-carriers that penetrate into the adventitia may remain in the adventitia layer for a prolonged time. In other words, the adventitia layer may act as a reservoir of the drug from where the drug is slowly released over the prolonged time.

The drug present in the nano-carrier of the two or more nano-carriers is released only after the nano-carriers penetrates one or more of the intima layer, the media layer and the adventitia layer and after the dissolution of the encapsulating medium. Thus, an in-tissue release of the drug at the target site is achieved. The drug thus released may diffuse across one or more of the adventitia layer, the media layer and the intima layer during the prolonged time. In such an instance, the drug that is diffused across the one or more of the adventitia layer, the media layer and the intima layer may provide an in-tissue diffusion of the drug for the prolonged time. Thus, because of the in-tissue release of the drug and the in-tissue diffusion of the drug, the drug may be delivered to maximum portion of a lesion at the target site.

In still yet another embodiment, the inflatable balloon is used to deliver the drug to a target site where a stent is deployed in the blood vessel. In such an instance, owing to the in-tissue release and in-tissue penetration of the drug for the prolonged time, the instances of delayed healing of lesions at the target site and improper healing of the lesions at the target site are minimized. Thus, an anti-platelet therapy that has to be given to the patients with delayed healing or improper healing of the lesions may be minimized.

In accordance with various embodiments, the two or more nano-carriers may be coated on the hydrophilic surface of the inflatable balloon in any manner so as to achieve a particular therapeutic objective without departing from the scope of the invention. The manners in which the two or more nano-carriers may be coated on the hydrophilic surface includes, one or more of, but are not limited to, coating the two or more nano-carriers as a single layer on the hydrophilic surface, coating the two or more nano-carriers as two or more layers on the hydrophilic surface and coating the two or more nano-carriers using one or more polymers. Further, the two or more nano-carriers may be coated on the hydrophilic surface of the inflatable balloon by using one or more techniques, for example, but are not limited to, spray-coating, deep-coating, ultrasonic cloud coating, mist coating, electrostatic coating and any other technique known in the art.

Generally speaking, pursuant to various embodiments, the invention also discloses a method for delivering the drug to the target site in a body lumen for treating the medical condition associated with the body lumen. The method includes positioning the inflatable balloon at the target site in the body lumen. The inflatable balloon may be positioned at the target site by using the balloon catheter assembly and the methods known in the art. After the inflatable balloon is positioned at the target site, the inflatable balloon is inflated using suitable inflating mechanism associated with the balloon catheter assembly. In response to the inflating, the inflatable balloon comes in contact with the target site and about 30% to 80% of the two or more nano-carriers are released from the inflatable balloon within 15 to 90 seconds upon contacting the target site. In accordance with various embodiments, the inflatable balloon may be brought into the contact with the target site for one or more times to deliver the drug to the target site.

EXAMPLE 1

Soya phospholipid was obtained from Lioid GMBH, Batch No.: 776114-1/906. Sirolimus was obtained from Fujan Chemicals, China with purity greater than 99.5%. The water, other solvents and reagents used were of HPLC grade. A polyamide catheter system with COPAN Co-Polyamide angioplasty balloon (herein after "the balloon system") coated with Hydraflow® Hydrophilic coating (hereinafter "the hydrophilic surface") was obtained from Minvasys, Paris, France.

Soya phospholipid (20 mg w/w) was added to HPLC grade water (20 ml) followed by Tween 80 (5 mg) to obtain aqueous solution of soya phospholipid. The aqueous solution of soya phospholipid (20 ml) was subjected to a high speed homogenization at 15000-20000 rpm for 20 to 25 minutes in ice-cold water bath to obtain Solution A1. The Solution A1 thus obtained contained nano-particles of soya phospholipid. The solution A1 was subsequently analyzed for particle size detection using Malvern ZS90 (Malvern, UK) size detector. FIG. 1 illustrates the size distribution of nano-particles of soya phospholipid as detected by Malvern ZS90. The average diameter of the nano-particles of the soya phospholipid was found to be 431 nm with largest diameter up to 1000 nm.

Sirolimus (20 mg w/w) was added to 10 ml of de-ionized water to obtain aqueous solution of sirolimus. The aqueous solution of sirolimus (10 ml) was subjected to a high speed homogenization at 15000-20000 rpm for 150 to 200 minutes in ice-cold water bath to obtain Solution A2. The Solution A2 thus obtained contained nano-crystals of sirolimus.

Figure 1:
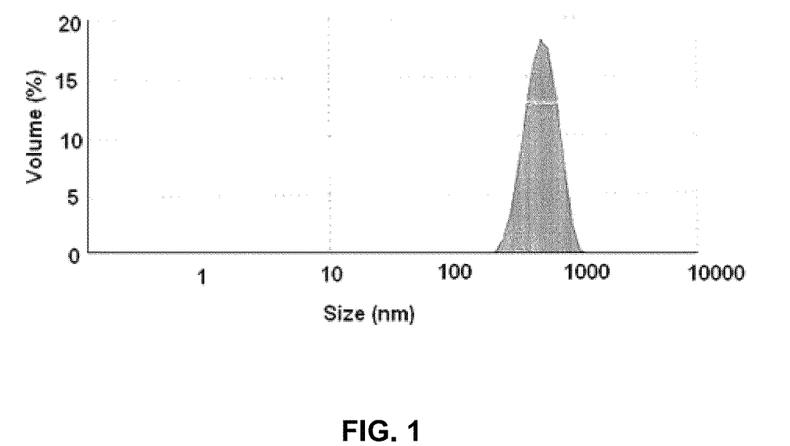
FIG. 1 illustrates the size distribution of nano-particles of soya phospholipid as detected by Malvern ZS90 in accordance with Example 1.
Figure 2:
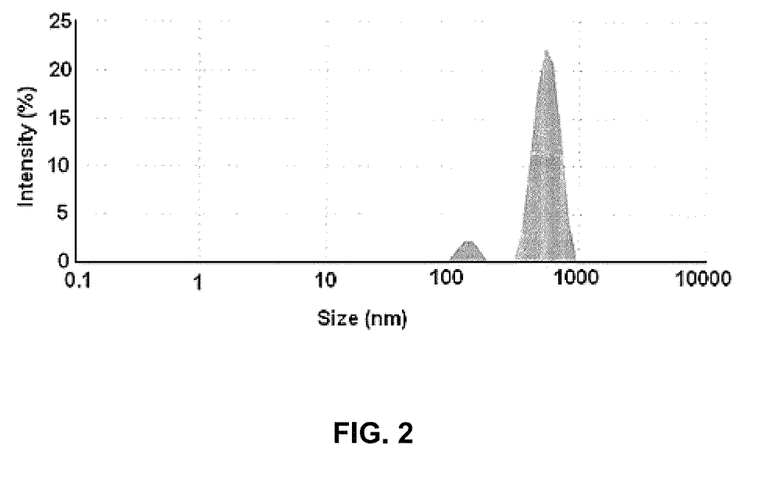
FIG. 2 illustrates the size distribution of nano-carriers as detected by Malvern ZS90 in accordance with Example 1.

Solution A1 was immediately added to Solution A2 drop by drop slowly under high speed homogenization process. The resultant mixture was subjected to a high speed homogenization at 15000-20000 rpm for another 20 minutes after complete addition to obtain Solution A3. Solution A3 was then stirred with a magnetic stirrer (2MLH hot plate heater cum stirrer, Accumax, INDIA) for 20 minutes. Solution A3 thus obtained contained nano-carriers (nano-crystals of sirolimus surrounded by nano-particles of soya phospholipid). Solution A3 was subsequently analyzed for particle size detection using Malvern ZS90 (Malvern, UK) size detector. FIG. 2 illustrates the size distribution of nano-carriers as detected by Malvern ZS90. The average diameters of nano-carriers were found to be 133.6 nm (Peak 1) and 554.9 nm (Peak 2) with maximum diameter being up to 1000 nm.

Solution A3 (Aqueous solution of nano-carriers) was further subjected to extraction with dichloromethane. Solution A3 (20 ml) was transferred to 100 ml separating funnel. 50 ml of dichloromethane was added to the 100 ml separating funnel. The resultant mixture was shaken for 15 min and then allowed to stand. Thereafter, two layers i.e. aqueous layer and the dichloromethane layer were observed in the 100 ml separating funnel. The dichloromethane layer was separated from the aqueous layer. The dichloromethane layer i.e. solution of the nano-carriers was stored in amber colored small measuring flask with batch number. Subsequently, the solution of the nano-carriers was used for coating the balloon system.

The solution of the nano-carriers (5 ml) was fed into the reservoir of a coating machine. The balloon system was mounted on a rotating mandrel of the coating machine. The balloon of the balloon system was exposed to the atomization nozzle of the coating machine. The balloon system was rotated at 5 to 40 rpm by rotating the mandrel and simultaneously the solution of nano-carriers was sprayed over the balloon at 0.5-4.0 psi inert gas pressure and 2 oscillations. Thus, the balloon coated with the nano-carriers (hereinafter "the coated balloon") was obtained. The coated balloon system was then removed and checked under high resolution microscope for the coating surface smoothness and any foreign particles. The coated balloon system was then subjected to further analysis as explained in Example 2 below.

EXAMPLE 2

Figure 3:
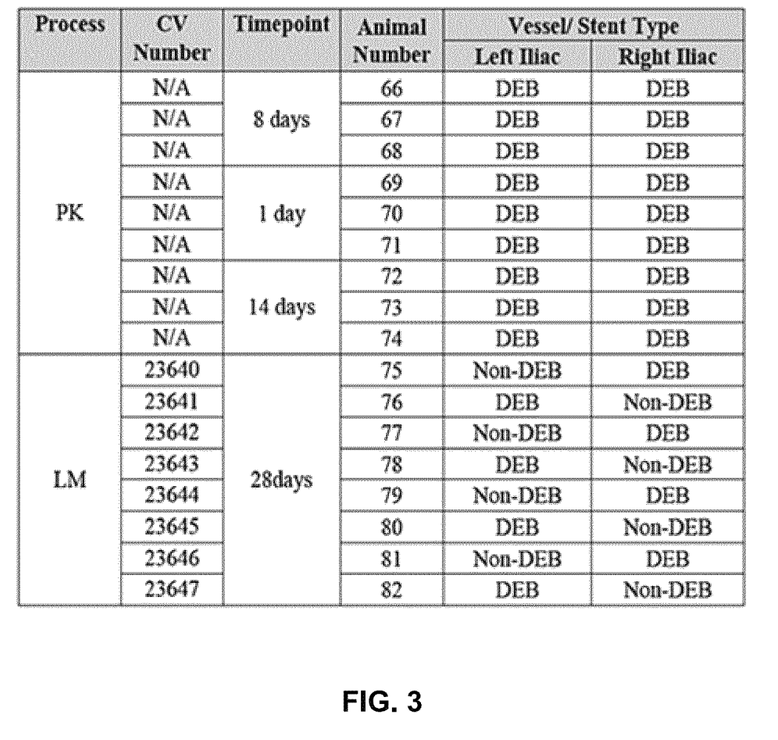
FIG. 3 is a table illustrating numbers assigned to 17 animals, stent type and location of stent in each animal and the type of study (PK/LM) conducted on the animals in accordance with Example 2.

The coated balloon was further evaluated in-vivo in 17 male New Zealand rabbits, 5 to 6 months old and weighing between 3 and 4 Kg (hereinafter "animals") for PharmacoKinetic (PK) study and histological evaluation or Light Microscopy (LM). FIG. 3 is a table illustrating numbers assigned to 17 animals, stent type and location of stent in each animal and the type of study (PK/LM) conducted on the animals. Out of the 17 animals 9 (Animals 66 to 74) were used for PK study and 8 (Animals 75 to 82) were used for histological evaluation.

The coated balloons were inserted into both the iliofemoral arteries of the animals used for the PK study. The coated balloons were inflated twice in the iliofemoral arteries. The coated balloons were first inflated for 70 seconds at 7 ATM and then deflated. Again, the coated balloons were inflated for the second time for 60 seconds at 7 ATM and then deflated and withdrawn.

A pre-mounted stent (3.0 mm×12-14 mm) i.e. a stent mounted on the coated balloon was implanted in the right and the left iliac artery of the animals at a nominal pressure with 30 seconds of balloon inflation. The balloon to stent ratio for all the pre-crimped stents was approximately 1.4:1. Following the deployment of the stents, angiography was performed to examine the patency of the stents.

Whole blood was collected from the central ear of the animals for serum analysis at four time points, namely 0.5 Hour, 1 Hour, 3 Hour and 24 Hour post deployment of the stents. After euthanasia at the respective time point, the tissue around the stent was dissected free, weighed, and snapfrozen in liquid nitrogen for later measurement. The University of Colorado Denver performed drug analysis of whole blood and the tissue surrounding the stent. The concentration of sirolimus at the four time points i.e. 0.5 Hour, 1 Hour, 3 Hour and 24 Hour was found to be 9.32 ng/ml, 7.08 ng/ml, 4.09 ng/ml and 0.81 ng/ml, respectively.

It was concluded that at Day 1, Day 8, and Day 14 pharmacokinetics study, maximal blood concentrations of sirolimus were seen at 30 minutes post catheterization (9.3 ng/ml) while circulating levels decreased markedly by 24 hours (0.81 ng/ml). For tissue drug levels, maximal concentrations were achieved at Day 1 (140.4 ng/mg), which showed a significant decreased to 15.5 ng/mg by Day 8 and 5.5 ng/mg by Day 14. Individual drug concentrations at each time point however, show variation among arteries where values at Day 1 ranged from 35.0 to 275.0 ng/mg, values at Day 8 ranged from 0.7 ng/mg to 33.2 ng/mg and values at Day 14 ranged from 14.8 ng/mg to below limits of quantification [BLQ] in two animals (Animal number 72 and 74). In comparison, published data in the rabbit with a sirolimus-eluting stent at similar time points achieved tissue concentrations of 4.52 ng/mg and 1.56 ng/mg at Day 1 and Day 8, respectively (Finn A V, Kolodgie F D *Circulation* 2005; 112:270).

Further measurements included histological study of the slides of the tissues around the stents. The slides were analyzed by using National Institute for Standard and Technology calibrated microscope system (IP Lab Software, MD). The cross-sectional areas for each slide i.e. External Elastic Lamina (EEL), Internal Elastic Lamina (IEL) and the Lumen Area were measured. Neointimal thickness was measured as a distance between the inner surface of the stent strut and the Luminal border of the stent. Vessel layer areas were calculated using the following formulae:

Area of Media=EEL−IEL,

Neointima Area=IEL−the Lumen Area and

Percent Stenosis=[1−(Luminal Area/IEL)]*100.

All the stents were found to be widely expanded and well apposed to the vessel walls. All the animals survived the in-life-phase of the study.

Re-endothelialization was found to be complete for the sample group and the control group. Percent Stenosis was found to be 11.48 (±1.30%) in sample group and 11.49 (±1.49%) in the control group. The Neointimal Thickness was found to be 0.030 mm (±0.0076 mm) in sample group and 0.032 (±0.0098 mm) in the control group.

In-tissue sirolimus concentration was also evaluated at Day 1, Day 8 and Day 14. The in-tissue sirolimus concentration at Day 1, Day 8 and Day 14 were found to be 140.4 ng/mg, 15.5 ng/mg and 5.5 ng/mg respectively. It was concluded that relatively higher in-tissue concentrations can be achieved with the coated balloon with single inflation as compared with the published data of study in rabbits pertaining a sirolimus-eluting stent with similar time points (Finn A V, Kolodgie F D *Circulation* 2005; 112:270).

EXAMPLE 3

6 Brazilian pigs (Hereinafter "the animals") weighing about 25 to 30 kg were selected for the study. Bare metal stent (Cronus®, obtained from, Scitech, Brazil), with sizes of stent ranging from 2.5*13 mm to 3.0*13 mm and the coated balloons with sizes of about 3.0*15 mm were used. The stents were deployed in three vessels i.e. LAD (Left Interior Descending), LCX (Left Circumflex) and RCA (Right Coronary Artery of each animal by using: a) the coated balloon (Sirolimus), b) the coated balloon (Paclitaxel) and c) a bare balloon. The Paclitaxel coated balloon was prepared by replacing sirolimus in example 1 with Paclitaxel and rest of the process was kept same. The balloon to artery ratio for each coated balloon was approximately 1.1:1.0 to 1.2:1.0. Each of the coated balloon and the bare balloon were inflated for 60 seconds. The animals with sirolimus coated balloon were labeled "Sirolimus", the animals with Paclitaxel coated balloon were labeled "Paclitaxel" and the animals with bare balloon were labeled "Control".

The groups i.e Sirolimus, Paclitaxel and Control were each studied for qualitative OCT analysis. The qualitative parameters that were studied included: a) Tissue Proliferation at the stent edges, b) Intra-luminal Thrombus Formation and c) Uncovered Stent Struts. It was found that the Tissue Proliferation at the stent edges was found in one Control and two Paclitaxel. Whereas, no incidence of Tissue Proliferation at the stent edges was observed in the Sirolimus group. Further, it was found that the Intra-luminal Thrombus Formation was found in one Control and two Paclitaxel. Whereas, no incidences of Intra-luminal Thrombus Formation were observed in the Sirolimus group.

It was concluded that sirolimus performed better than paclitaxel and bare balloon in terms of reduction in neointimal growth and endothelialization. The stent strut coverage by tissue was virtually complete for all the groups. Toxic effect was found in paclitaxel group. The toxic effect was found in the paclitaxel group due to greater in-tissue concentration of paclitaxel. However, the dose of the paclitaxel used was lower as compare with commercially available products. Thus, the coated balloons showed acute transfer of paclitaxel or sirolimus using a polymer free approach.

Figure 4:
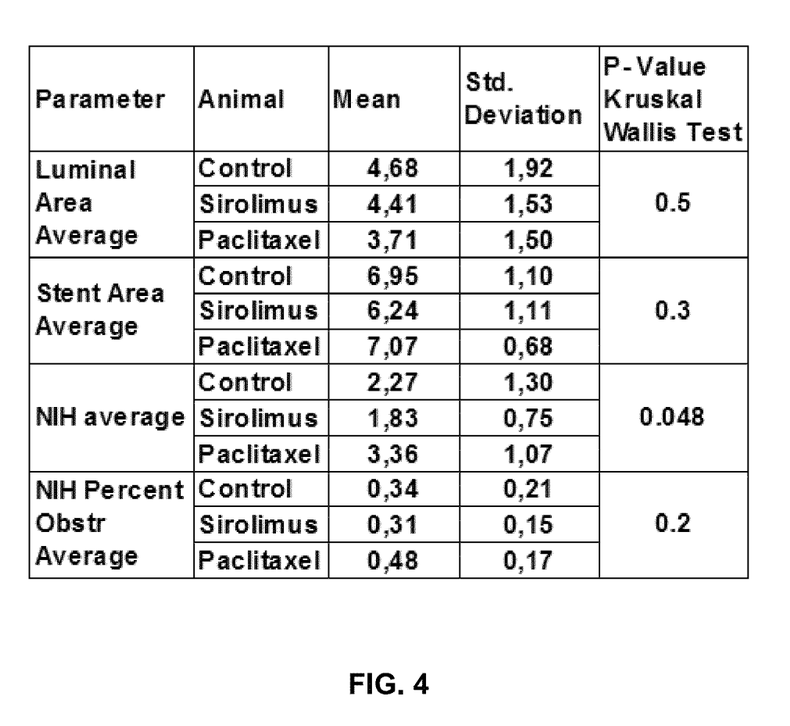
FIG. 4 illustrates a table of values of mean and standard derivations of the Average Luminal Areas, Average Stent Areas, Average Neointimal Areas and Average Percent Neointimal Obstruction findings for each group i.e. Control, Sirolimus and Paclitaxel in accordance with Example 3.
Figure 5:
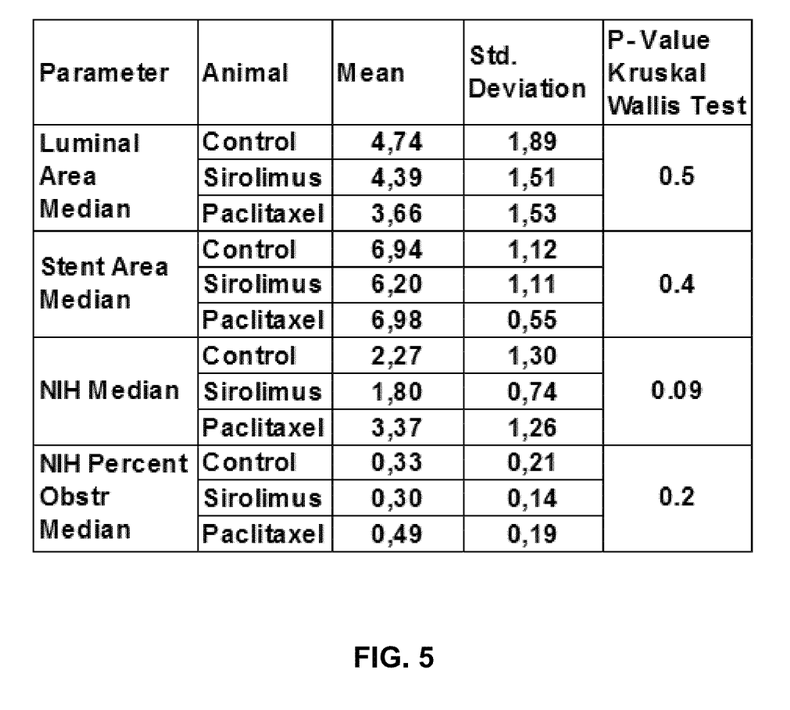
FIG. 5 illustrates a table of values of mean and standard derivations of the Median Luminal Areas, Median Stent Areas, Median Neointimal Areas and Median Percent Neointimal Obstruction findings for each group in accordance with Example 3.
Figure 6:
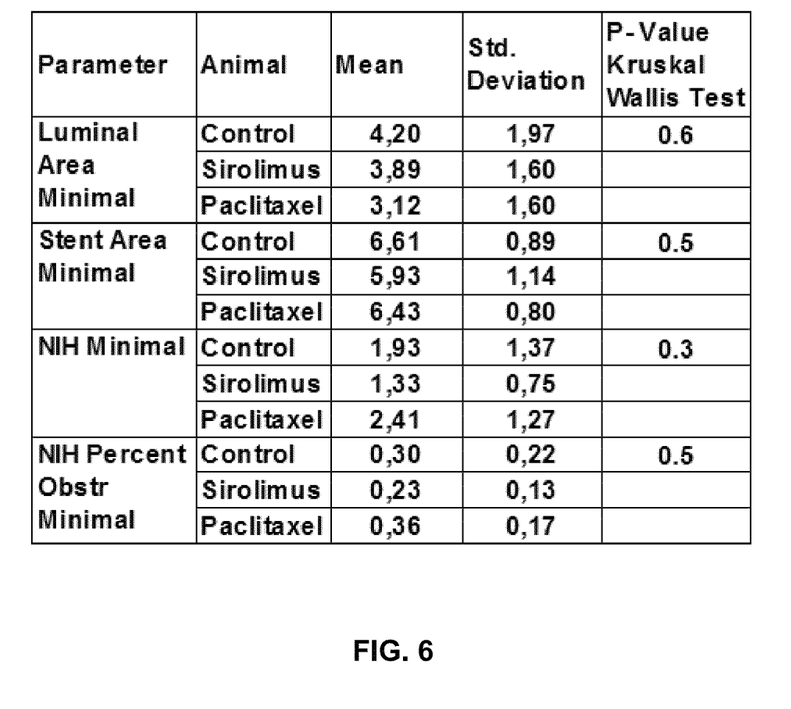
FIG. 6 illustrates a table of values of mean and standard derivations of the Minimal Luminal Areas, Minimal Stent Areas, Minimal Neointimal Areas and Minimal Percent Neointimal Obstruction findings for each group in accordance with Example 3.
Figure 7:
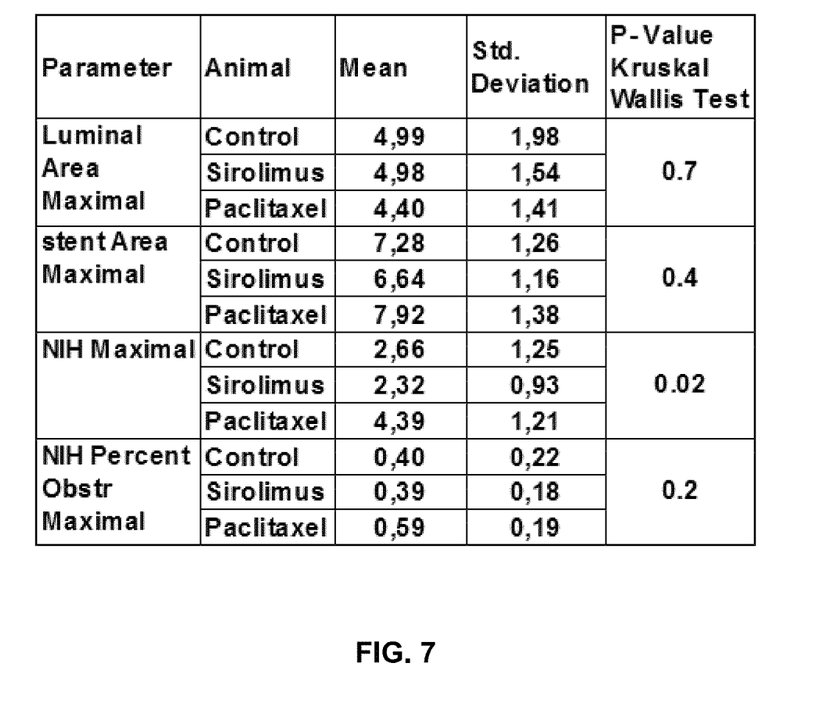
FIG. 7 illustrates a table of values of mean and standard derivations of the Maximal Luminal Areas, Maximal Stent Areas, Maximal Neointimal Areas and Maximal Percent Neointimal Obstruction findings for each group in accordance with Example 3.
Figure 8:
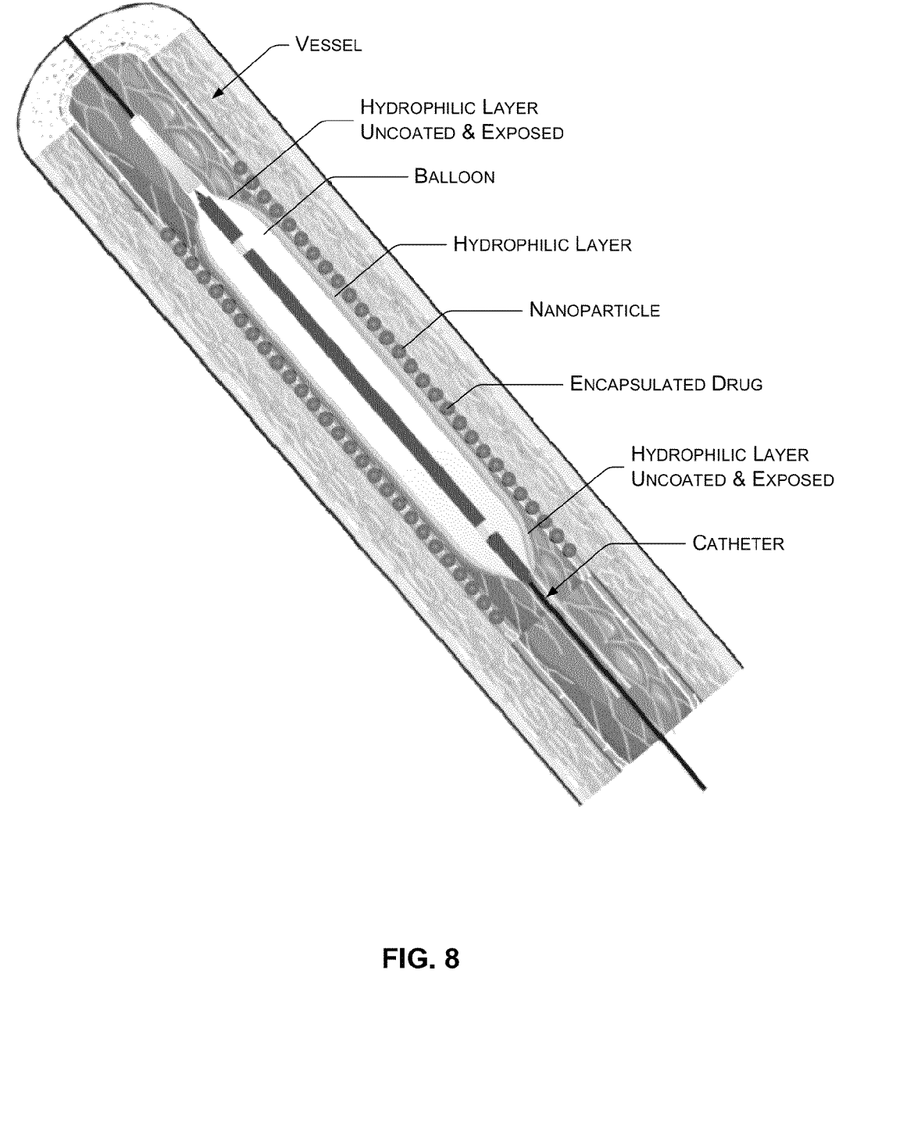
FIG. 8 is a diagram of a drug-delivering medical device shown in a body lumen, that includes a balloon catheter, an inflatable balloon positioned on the balloon catheter, the inflatable balloon having a hydrophilic surface, at least one portion of the hydrophilic surface being coated with a plurality of nano-carriers (nano-carriers not shown to scale), with at least one of the nano-carriers surrounded by an encapsulating medium.

Quantitative OCT analysis was performed on six equidistant in-stent tissue slices for each stent. Thus a total of 108 [i.e. 6 (animals)*3 (arteries each)*6 (tissue slices)] in-stent tissue slices (cross-sections) were analyzed. The parameters for quantitative analysis included: a) Lumen Area, b) Stent Area, c) Neointimal Area and d) Percent Neointimal Obstruction. FIG. 4 illustrates a table of values of mean and standard derivations of the Average Luminal Areas, Average Stent Areas, Average Neointimal Areas and Average Percent Neointimal Obstruction findings for each group i.e. Control, Sirolimus and Paclitaxel. FIG. 5 illustrates a table of values of mean and standard derivations of the Median Luminal Areas, Median Stent Areas, Median Neointimal Areas and Median Percent Neointimal Obstruction findings for each group. FIG. 6 illustrates a table of values of mean and standard derivations of the Minimal Luminal Areas, Minimal Stent Areas, Minimal Neointimal Areas and Minimal Percent Neointimal Obstruction findings for each group. FIG. 7 illustrates a table of values of mean and standard derivations of the Maximal Luminal Areas, Maximal Stent Areas, Maximal Neointimal Areas and Maximal Percent Neointimal Obstruction findings for each group. It was concluded that out of a data set of the 927 stent struts, just one strut (Paclitaxel) was found to be unequivocally uncovered by the tissues. Based on observation of thrombus it was concluded that drug dose of paclitaxel might be higher than required. The higher dose and vis-a-vis the thrombus effect of the paclitaxel may be attributed to higher in-tissue drug penetration of paclitaxel. Thus the amount of sirolimus of paclitaxel to be coated on the coated balloon is lesser than the amount of sirolimus of paclitaxel loaded on current DEBs.

Various embodiments of the invention provide a drug-delivering balloon that can efficiently deliver the drug to the target site in the blood vessel within a short period for which the drug-delivering balloon comes in contact with the target site. In addition, the invention provides a drug-delivering balloon that can efficiently deliver drug to the maximum area of a lesion and provide for enhance bioavailability with an optimum amount of the drug loaded on the drug-delivering balloon.

Those skilled in the art will realize that the above-recognized advantages and other advantages described herein are merely exemplary and are not meant to be a complete rendering of all of the advantages of the various embodiments of the invention.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The present invention is defined solely by the appended claims including any amendments made during the pendency of this application and all equivalents of those claims as issued.

What is claimed is:

1. A drug-delivering medical device for delivering agents to treat a target site via a blood vessel, comprising:
  a balloon catheter; and
    an inflatable balloon positioned on the balloon catheter, the inflatable balloon having a hydrophilic surface,
    at least one portion of the hydrophilic surface being coated with a plurality of nano-carriers, including:
  a first set of nano-carriers comprising a pro-healing agent,
  a second set of nano-carriers comprising an anti-proliferative agent, and a third set of nano-carriers comprising one or both of an anti-inflammatory agent and an anti-thrombogenic agent,
  the first set of nano-carriers having a first average diameter ranging from 800 nm to 1500 nm suitable for penetrating an intima layer of a blood vessel through inter-tissue pores present in the intima layer,
  the second set of nano-carriers having a second average diameter ranging from 300 nm to 800 nm suitable for penetrating a media layer of the blood vessel through a vasa vasorum associated with the media layer and the inter-tissue pores present in the intima layer, and
  the third set of nano-carriers having a third diameter ranging from 10 nm to 300 nm suitable for penetrating an adventitia layer of the blood vessel through the inter-tissue pores present in the intima layer, the vasa vasorum associated with the media layer and a vasa vasorum associated with the adventitia layer;

wherein a first time required for the third set of nano-carriers to release from the hydrophilic surface upon coming in proximity of the target site is less than a second time required for the second set of nano-carriers and the first set of nano-carriers to release from the hydrophilic surface;

wherein the third set of nano-carriers exhibit a rapid rate of release from the hydrophilic surface and wherein the second set of nano-carriers and the first set of nano-carriers exhibit slower rates of release from the hydrophilic surface as compared with the rate of release of the third set of nano-carriers;

at least one adjacent portion of the hydrophilic surface being uncoated and exposable to a blood or a tissue environment for rapid dissolution from the inflatable balloon and for rapid dissolution from underneath the nano-carriers of an adjacent coated portion of the hydrophilic surface, the rapid dissolution from underneath providing an increase in the rapidity of release of the nano-carriers of the adjacent coated portion;

each nano-carrier of the plurality of nano-carriers comprising a respective agent surrounded by an encapsulating medium, wherein a surface of each nano-carrier is devoid of the respective agent and 30% to 80% of the plurality of the nano-carriers are released from the hydrophilic surface within 15-90 seconds when the inflatable balloon is inflated upon coming in proximity to the target site in the blood vessel; and wherein the third set of nano-carriers penetrating into the adventitia layer remain in the adventitia layer for a prolonged time and act as a reservoir of the one or both of the anti-inflammatory agent and the anti-thrombogenic agent to slowly release the one or both of the anti-inflammatory agent and the anti-thrombogenic over the prolonged time.

2. The drug-delivering medical device of claim 1, wherein the encapsulating medium comprises at least one of a biological agent, a phospholipid and a blood excipient.

3. The drug-delivering medical device of claim 1, wherein the inflatable balloon has a distal end and a proximal end and at least a portion of the distal end of the inflatable balloon and at least a portion of the proximal end of the inflatable balloon are not coated with the plurality of nano-carriers.

4. The drug-delivering medical device of claim 2, wherein the biological agent and the phospholipid have at least one effect selected from a group comprising affinity for the target site and stabilizing the drug.

5. The drug-delivering medical device of claim 2, wherein the biological agent dissolves in a medium having a pH less than 7.4.

6. The drug-delivering medical device of claim 2, wherein the at least one biological agent is selected from a group comprising drug carriers, excipients, blood components, excipients derived from blood, phospholipids, solid lipid nano-particles, lipids, vitamins and sugar molecules.

7. The drug-delivering medical device of claim 2, wherein the biological agent is selected from a group comprising steroids, vitamins, estradiol, esterified fatty acids, non-estrified fatty acids, glucose, inositol, L-lactate, lipoproteins, carbohydrates, tricalcium phosphate, precipitated calcium phosphate, calcium phoshate tribasic, substances derived from at least one of human, egg and soybean, phospholipon 80H, phospholipon 90H, Lipoids S75, Lipoids E80, Intralipid 20, Lipoid EPC, Lipoids E75, lipids obtained from egg, lipids obtained from soya, phosphatidylcholine, phosphatidylglycerol, phosphatidylinositol, phosphatidylserine, phosphatidic acid, cardiolipin, and phosphatidylethanolamine.

8. The drug-delivering medical device of claim 1, wherein one of the agents is selected from a group comprising anti-proliferative agents, anti-inflammatory agents, anti-neoplastic agents, anti-coagulant agents, anti-fibrin agents, anti-thrombotic agents, anti-mitotic agents, antibiotic agents, anti-allergic agents and antioxidants, at least one flavonoid, estrogen, protease inhibitors, antibodies, immunosuppressive agents, cytostatic agents, cytotoxic agents, calcium channel blockers, phosphodiesterase inhibitors, prostaglandin inhibitors, dietary supplements, vitamins, anti-platelet aggregating agents and genetically engineered epithelial cells, wherein the at least one flavonoid is selected from a group comprising at least one of narigenin, naringin, eriodictyol, hesperetin, hesperidin (esperidine), kampferol, quercetin, rutin, cyanidol, meciadonol, catechin, epi-gallocatechin-gallate, taxifolin (dihydroquercetin), genistein, genistin, daidzein, biochanin, glycitein, chrysin, diosmin, luetolin, apigenin, tangeritin and nobiletin.

9. The drug-delivering medical device of claim 1, wherein one of the agents is selected from a group comprising sirolimus, paclitaxel, tacrolimus, clobetasol, dexamethasone, genistein, heparin, beta-estadiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin, sodium heparin, low molecular weight heparin, heparinoid, hirudin, argatroban, forskolin, vapiprost, prostacyclin, prostacyclin analogues, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, serotonin blockers, a steroid, thioprotease inhibitors, triazolopyrimidine, nitric oxide, nitric oxide donors, super oxide dismutase, super oxide dismutase mimetics, estradiol, aspirin, angiopeptin, captopril, cilazapril, lisinopril, permirolast potassium, alpha-interferon, and bioactive RGD.

10. The drug-delivering medical device of claim 1, wherein one of the agents is selected from a group comprising Sirolimus and Paclitaxel.

11. The drug-delivering medical device of claim 1, wherein the inflatable balloon is sized to contact an inner surface of the body lumen upon inflation.

12. The drug-delivering medical device of claim 1, wherein the drug-delivering medical device is used to treat a medical condition, wherein the medical condition is selected from of a group comprising stenosis, restenosis, blockages in an artery, thrombus in artery, acute myocardial infarction, and arterial lesions.

* * * * *